US012658297B2

(12) United States Patent
Bartlett et al.

(10) Patent No.: US 12,658,297 B2
(45) Date of Patent: Jun. 16, 2026

(54) MEDICAL ITEM RESUPPLY ENGINE AND ENGAGEMENT CONTROLLER

(71) Applicant: Brightree LLC, Peachtree Corners, GA (US)

(72) Inventors: Gary Allen Bartlett, Bradenton, FL (US); Cinthia Herschberg Wright, Nashville, TN (US); Michael A. Lorenz, Brentwood, TN (US); Nupura Kolwalkar, Cumming, GA (US)

(73) Assignee: Brightree LLC, Peachtree Corners, GA (US)

( * ) Notice: Subject to any disclaimer, the term of this patent is extended or adjusted under 35 U.S.C. 154(b) by 0 days.

(21) Appl. No.: 18/820,954

(22) Filed: Aug. 30, 2024

(65) Prior Publication Data

US 2024/0420815 A1     Dec. 19, 2024

Related U.S. Application Data

(63) Continuation of application No. 17/934,748, filed on Sep. 23, 2022, now Pat. No. 12,119,097, and a continuation of application No. 17/934,888, filed on Sep. 23, 2022.

(51) Int. Cl.
*G16H 20/00* (2018.01)

(52) U.S. Cl.
CPC .................................... *G16H 20/00* (2018.01)

(58) Field of Classification Search
CPC ............................... G16H 20/00; G16H 40/20
See application file for complete search history.

(56) References Cited

U.S. PATENT DOCUMENTS

| | | | |
|---|---|---|---|
| 10,783,082 B2 | 9/2020 | Yao | |
| 10,802,854 B2 | 10/2020 | Liu | |
| 10,855,448 B2 * | 12/2020 | McMurdie | ............ H04L 9/3263 |
| 10,929,570 B2 * | 2/2021 | Zou | ......................... G06F 21/64 |
| 11,010,303 B2 | 5/2021 | Yao | |
| 11,138,345 B2 | 10/2021 | Zou et al. | |
| 11,138,600 B2 | 10/2021 | Abad et al. | |
| 11,184,175 B2 | 11/2021 | Soundararajan et al. | |
| 11,233,641 B2 | 1/2022 | Soundararajan et al. | |

(Continued)

OTHER PUBLICATIONS

Braunstein, Mark L., "Health Informatics on FHIR: How HL7's New API is Transforming Healthcare", 'Springer, 2018.

(Continued)

*Primary Examiner* — Robert A Sorey
*Assistant Examiner* — Kristine K Rapillo
(74) *Attorney, Agent, or Firm* — Patterson + Sheridan, LLP

(57) ABSTRACT

Techniques for improved resupply for medical items are provided. An event relating to resupply of one or more medical items for a patient is identified, where the resupply requires approval from a physician. Based on the event, a request for electronic approval of the resupply is transmitted to an electronic healthcare system for the physician. In response to the request, an indication of failure of electronic approval of the resupply is received. Based on the indication of failure, resupply of the one or more medical items is not initiated, and a cause for the failure of electronic approval of the resupply is determined based on parsing a textual indication included in the response to the request using natural language processing (NLP).

20 Claims, 13 Drawing Sheets

100 —

(56) References Cited

U.S. PATENT DOCUMENTS

| 11,245,525 | B2 | | 2/2022 | Roongta et al. |
| 11,250,466 | B2 | | 2/2022 | Soundararajan et al. |
| 11,265,162 | B2 | | 3/2022 | Yang et al. |
| 11,270,403 | B2 | | 3/2022 | Soundararajan et al. |
| 11,271,908 | B2 | | 3/2022 | Soundararajan et al. |
| 11,283,872 | B1 | | 3/2022 | Jayapalan |
| 11,289,196 | B1 | | 3/2022 | Ferro, Jr. et al. |
| 11,301,807 | B2 | | 4/2022 | Hill et al. |
| 11,307,990 | B2 | * | 4/2022 | Yao .......................... H04L 63/12 |
| 11,356,443 | B2 | * | 6/2022 | Soundararajan .... H04L 63/0815 |
| 11,367,045 | B2 | * | 6/2022 | Hill ......................... G06F 16/27 |
| 11,367,530 | B1 | | 6/2022 | Ferro, Jr. et al. |
| 11,369,454 | B1 | | 6/2022 | Ferro, Jr. et al. |
| 11,373,756 | B1 | | 6/2022 | Ferro, Jr. et al. |
| 11,393,586 | B1 | * | 7/2022 | Ferro, Jr. .............. A61B 5/7267 |
| 11,397,905 | B2 | * | 7/2022 | Hill .................... G06Q 10/0631 |
| 11,403,674 | B2 | * | 8/2022 | Soundararajan .......... H04L 9/50 |
| 11,410,773 | B2 | * | 8/2022 | Ferro, Jr. ................. G09B 7/00 |
| 11,488,160 | B2 | * | 11/2022 | Soundararajan ..... G06Q 20/389 |
| 11,488,161 | B2 | * | 11/2022 | Soundararajan ....... G06Q 20/06 |
| 11,515,037 | B2 | * | 11/2022 | Ferro, Jr. .............. G16H 20/10 |
| 2002/0069087 | A1 | * | 6/2002 | Fairley ................... G06Q 10/10 |
| | | | | 705/2 |
| 2010/0161345 | A1 | | 6/2010 | Cain et al. |
| 2020/0101367 | A1 | * | 4/2020 | Tran ...................... A63B 71/06 |
| 2023/0326584 | A1 | * | 10/2023 | Nadelson .............. G16H 10/20 |
| | | | | 705/2 |

OTHER PUBLICATIONS

Trenfield, et al., "Advancing Pharmacy and Healthcare with Virtual Digital Technologies", Advanced Drug Delivery Reviews 182, 2022.

* cited by examiner

400

MEDICAL ITEM RESUPPLY ENGINE AND ENGAGEMENT CONTROLLER

CROSS-REFERENCE TO RELATED APPLICATIONS

This application claims priority to U.S. Non-Provisional patent application Ser. No. 17/934,748 and U.S. Non-Provisional patent application Ser. No. 17/934,888, both filed Sep. 23, 2022, the entire contents of which are incorporated herein by reference in their entirety.

Introduction

Aspects of the present disclosure relate to patient medical care, and more specifically, to improved resupply for medical items, and improved engagement with patients and care providers.

Many medical patients have consumable medical items that must be resupplied. This can include items which must be prescribed by a physician, including a variety of home medical equipment (HME) (e.g., partially reusable or disposable HME) and prescription medications. The patients must be periodically resupplied with these consumable items. But this is a very challenging process, typically requiring manual intervention from a care provider to the patient. This results in poor patient outcomes, because difficulty in resupply can result in patients prematurely ending the associated medical treatment. It also results in increased expenses for patients, health insurers, and care providers and entities.

SUMMARY

Embodiments include a computer-implemented method. The method includes identifying an event relating to resupply of one or more medical items for a patient. The resupply requires approval from a physician. The method further includes transmitting, based on the event, a request for electronic approval of the resupply to an electronic healthcare system for the physician, including dynamically generating an electronic document relating to the required approval, providing the electronic document to the electronic healthcare system for the physician, and receiving an electronic message response from the electronic healthcare system for the physician indicating approval for the request. The electronic healthcare system for the physician is compatible with the request for electronic approval of the resupply. The method further includes initiating, based on the response, resupply of the one or more medical items. The one or more medical items are used to treat the patient.

Embodiments further include an apparatus including a memory and a hardware processor communicatively coupled to the memory, the hardware processor configured to perform operations. The operations include identifying an event relating to resupply of one or more medical items for a patient. The resupply requires approval from a physician. The operations further include transmitting, based on the event, a request for electronic approval of the resupply to an electronic healthcare system for the physician, including dynamically generating an electronic document relating to the required approval, providing the electronic document to the electronic healthcare system for the physician, and receiving an electronic message response from the electronic healthcare system for the physician indicating approval for the request. The electronic healthcare system for the physician is compatible with the request for electronic approval of the resupply. The operations further include initiating, based on the response, resupply of the one or more medical items. The one or more medical items are used to treat the patient.

Embodiments further include a non-transitory computer-readable medium including instructions that, when executed by a processor, cause the processor to perform operations. The operations include identifying an event relating to resupply of one or more medical items for a patient. The resupply requires approval from a physician. The operations further include transmitting, based on the event, a request for electronic approval of the resupply to an electronic healthcare system for the physician, including dynamically generating an electronic document relating to the required approval, providing the electronic document to the electronic healthcare system for the physician, and receiving an electronic message response from the electronic healthcare system for the physician indicating approval for the request. The electronic healthcare system for the physician is compatible with the request for electronic approval of the resupply. The operations further include initiating, based on the response, resupply of the one or more medical items. The one or more medical items are used to treat the patient.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
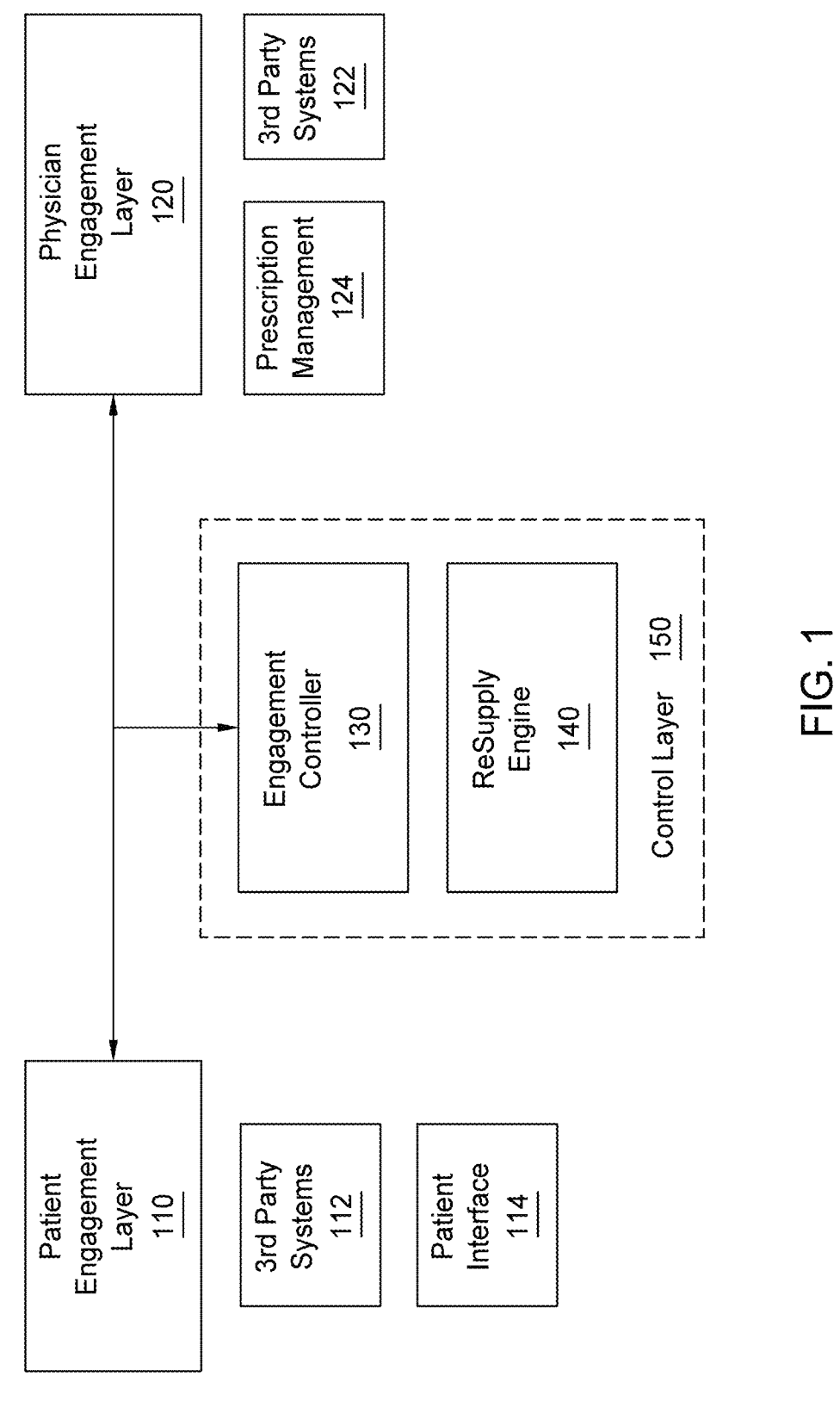
FIG. 1 depicts a computing environment for an automated medical resupply engine and engagement controller, according to one embodiment.

Aspects of the present disclosure provide apparatuses, methods, processing systems, and computer-readable mediums for improved medical resupply. As discussed above, resupply of consumable or disposable medical items, particularly prescription medical items, is very challenging. Existing systems require significant manual intervention from patients, physicians, and other care providers, which results in poor patient outcomes and significant inefficiencies.

One or more techniques disclosed herein relate to automated medical resupply, using a resupply engine, and patient and physician engagement systems. In an embodiment, a need for resupply for a patient can be automatically identified. For example policy rules (e.g., insurance policy rules, medical care policy rules, and any other suitable policy rules) and historical resupply order data can be used to identify when a patient is due for resupply. A resupply engine can then automatically trigger a resupply event to initiate the resupply. This can be done with no patient interaction, or with very limited patient interaction (e.g., with a simple approval request to the patient). Alternatively, or in addition, a patient can directly initiate resupply. For example, a patient can use a suitable user interface to request automatic resupply.

In an embodiment, this resupply event requires approval from a physician (e.g., it requires prescription items). In existing systems, this approval would be manually provided to the physician (e.g., through manual identification of the physician and transmission of a facsimile of the request to the physician). This is both extremely inefficient, because of the required manual intervention, and prone to failure, because a physician may not receive the facsimile or may not respond to the facsimile.

One or more techniques described herein automate the physician interaction to fulfill a resupply request (e.g., to eliminate, or significantly reduce, required human intervention). For example, a dynamic document can be generated from the resupply request. An approving physician can be automatically identified, and the dynamic document can be automatically transmitted to the physician. The physician can then use seamless electronic document signature tools to approve (or reject), the resupply request. If the request is approved it can be automatically fulfilled, without any additional intervention. Further, if the request is not approved the patient can automatically be provided with a notification of the failure and an indication of the reason for the failure.

In an embodiment, one or more of these techniques both significantly improve treatment of patients and provide technical improvements to existing electronic health systems. For example, the piecemeal and complex nature of existing systems can result in patients failing to timely request resupply, and in physicians failing to timely approve resupply requests. This can lead to patients running out of consumable medical items, forcing patients to discontinue treatment. Discontinuing treatment for the patients can worsen patient health outcomes and harm patient treatment. One or more techniques disclosed herein improve patient health outcomes by automating resupply requests, allowing for seamless physician approval of resupply requests, and automating fulfilment of approved resupply requests.

Further, one or more techniques disclosed herein provide for prophylactic treatment of patients. By identifying patients that are due for an upcoming resupply, and seamlessly fulfilling the resupply, these techniques can prophylactically avoid patients discontinuing treatment. This can keep patients engaged in treatment longer, improving their health outcomes. Further, alerting patients of an upcoming resupply can prompt patients that might otherwise be at risk of discontinuing treatment, to continue treatment. Automatically triggering, and fulfilling, resupply requests can both make it easier for patients positively engaged in treatment to continue treatment, and encourage patients at risk of discontinuing treatment to continue treatment (e.g., because necessary supplies are automatically identified and provided).

Further, existing electronic health systems do not provide for end to end engagement from a patient to a physician, for resupply. These systems can require computationally complex, and inefficient, analysis to communicate with patients and physicians across incompatible systems. For example, a patient may manually initiate a resupply request in an electronic system, but the system may not be able to contact the physician or complete the request (e.g., because of incompatibilities across the system). This results in wasted computational resources for the unfulfilled request, and potential failure by the system to complete the request. One or more techniques disclosed herein allow for seamless interaction from a patient to a physician and a resupply engine, reducing computational waste and reducing system failure. For example, one or more techniques disclosed herein provide improvements to electronic healthcare systems by verifying the compatibility of relevant electronic healthcare systems (e.g., patient related and physician related systems) and proceeding with automating resupply requests only for compatible systems.

FIG. 1 depicts a computing environment 100 for an automated medical resupply engine and engagement controller, according to one embodiment. In an embodiment the computing environment 100 includes a patient engagement layer 110. The patient engagement layer 110 facilitates engagement with a patient (e.g., through electronic transmissions, telephone calls, and any other suitable techniques) for automated medical resupply. This is discussed further with regard to FIGS. 10-11, below.

For example, the patient engagement layer 110 can facilitate transmitting electronic messages (e.g., short message service (SMS) messages, multimedia messaging service messages (MMS), e-mail messages, or any other suitable electronic messages) to a patient, and receiving electronic messages from a patient, to facilitate automated medical resupply. This is merely one example. In an embodiment, the patient engagement layer 110 interacts with one or more third party systems 112, a patient interface 114 (e.g., an electronic interface to communicate with a patient), and any other suitable components.

In an embodiment, the patient engagement layer 110 communicates with a control layer 150 including an engagement controller 130 and a resupply engine 140. For example, the engagement controller 130 can control patient engagement to facilitate automated medical resupply. The engagement controller 130 is discussed further, below, with regard to FIG. 2. In an embodiment, the patient engagement layer 110 communicates with the engagement controller 130 using a suitable communication network, including the Internet, a wide area network, a local area network, or a cellular network, and uses any suitable wired or wireless communication technique (e.g., WiFi or cellular communication).

In an embodiment the computing environment 100 further includes a physician engagement layer 120. The physician engagement layer 120 facilitates engagement with a physician (e.g., through electronic transmissions to an electronic healthcare system, telephone calls, and any other suitable techniques) for automated medical resupply. This is discussed further with regard to FIGS. 3-9, below.

For example, the physician engagement layer 120 can facilitate automated medical resupply of prescription items by creating necessary dynamic documents, and presenting the documents to physicians for review and electronic signature. This is merely one example. In an embodiment, the physician engagement layer 120 interacts with one or more third party systems 122, a prescription management system 124 (e.g., an electronic prescription management system), and any other suitable components.

In an embodiment, the physician engagement layer 120 communicates with the engagement controller 130. For example, the engagement controller 130 can control physician engagement to facilitate automated medical resupply. In an embodiment, the physician engagement layer 120 communicates with the engagement controller 130 using a suitable communication network, including the Internet, a wide area network, a local area network, or a cellular network, and uses any suitable wired or wireless communication technique (e.g., WiFi or cellular communication).

In an embodiment, the engagement controller 130 interacts with the resupply engine 140. For example, the resupply engine 140 can interact with the engagement controller 130 to generate resupply events and facilitate resupply. This can include facilitating all suitable aspects of resupply, including ordering, shipping, billing, and any other suitable tasks. For example, the engagement controller 130 can control interactions with the patient engagement layer 110 and physician engagement layer 120 to initiate, and complete, resupply orders using the resupply engine 140. These are merely examples, and the engagement controller 130 and resupply engine 140 can respectively perform any suitable tasks or combinations of tasks. For example, the engagement controller 130 and resupply engine 140 can be combined together to control both engagement (e.g., with patients and physicians) and resupply. As another example, the resupply engine 140 can interact directly with the patient engagement layer 110 and the physician engagement layer 120 (e.g., without the engagement controller 130).

In an embodiment, the engagement controller 130 can identify how to contact a particular patient or physician through queries to the patient engagement layer 110 and physician engagement layer 120. For example, a patient engagement layer 110 can relate to multiple different healthcare entities with a large number of patients. The engagement controller 130 can determine how to contact a particular patient by querying each electronic healthcare system associated with the patient engagement layer (e.g., using a suitable identifier or identifiers associated with the patient), and receiving a response from the electronic healthcare system related to the patient (e.g., the patient's insurer, healthcare provider, or any other suitable healthcare entity). In an embodiment, the engagement controller 130 can determine whether the electronic healthcare system related to the patient engagement layer 110 is compatible with the control layer 150 (e.g., with the engagement controller 130, the resupply engine 140, or both). The engagement controller 130 can decline to interact further with an incompatible patient engagement layer 110. An electronic healthcare system that does not recognize the requested patient will not respond, or will respond with an indication that the patient is not recognized. An electronic healthcare system that recognizes the patient will respond with an indication that the patient is successfully recognized. The engagement controller 130 can use that successful response to determine how to engage with the patient in the future.

Similarly, the engagement controller 130 can determine how to contact a particular physician by querying each electronic healthcare system associated with the physician engagement layer (e.g., using a suitable identifier or identifiers associated with the physician, including a national provider identifier (NPI)), and receiving a response from the electronic healthcare system related to the physician (e.g., a healthcare entity where the physician works). In an embodiment, the engagement controller 130 can determine whether the electronic healthcare system related to the physician engagement layer 120 is compatible with the control layer 150 (e.g., with the engagement controller 130, the resupply engine 140, or both). The engagement controller 130 can decline to interact further with an incompatible physician engagement layer 120. In an embodiment, an electronic healthcare system that does not recognize the requested physician will not respond, or will respond with an indication that the physician is not recognized. An electronic healthcare system that recognizes the physician will respond with an indication that the physician is successfully recognized. The engagement controller 130 can use that successful response to determine how to engage with the physician in the future.

In an embodiment, the engagement controller 130 interacts with a single patient engagement layer 110 and a single physician engagement layer 120 (e.g., each associated with multiple healthcare entities). Alternatively, or in addition, the engagement controller 130 can interact with multiple patient engagement layers 110 (e.g., each associated with a particular healthcare entity or small number of healthcare entities), multiple physician engagement layers 120 (e.g., each associated with a particular healthcare entity or small number of healthcare entities), or both. In this example, the engagement controller 130 can query multiple patient engagement layers 110 and multiple physician engagement layers 120, as appropriate, to determine how to contact the respective patient and physician.

In an embodiment the patient engagement layer 110, the physician engagement layer 120, the engagement controller 130, and the resupply engine 140, can be implemented using any suitable combination of physical compute systems, cloud compute nodes and storage locations, or any other suitable implementation. For example, the patient engagement layer 110, the physician engagement layer 120, the engagement controller 130, and the resupply engine 140 could each be implemented using a respective server or cluster of servers. As another example, the patient engagement layer 110, the physician engagement layer 120, the engagement controller 130, and the resupply engine 140 can be implemented using a combination of compute nodes and storage locations in a suitable cloud environment. For example, one or more of the components of the patient engagement layer 110, the physician engagement layer 120, the engagement controller 130, and the resupply engine 140 can be implemented using a public cloud, a private cloud, a hybrid cloud, or any other suitable implementation.

Figure 2:
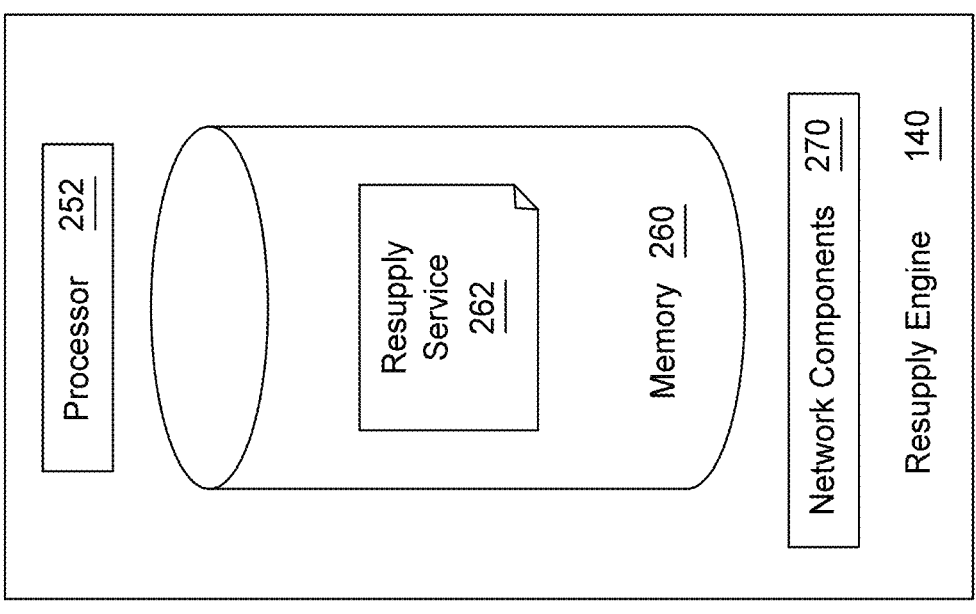
FIG. 2 depicts a block diagram for an engagement controller to interact with an automated resupply engine, according to one embodiment.
Figure 2:
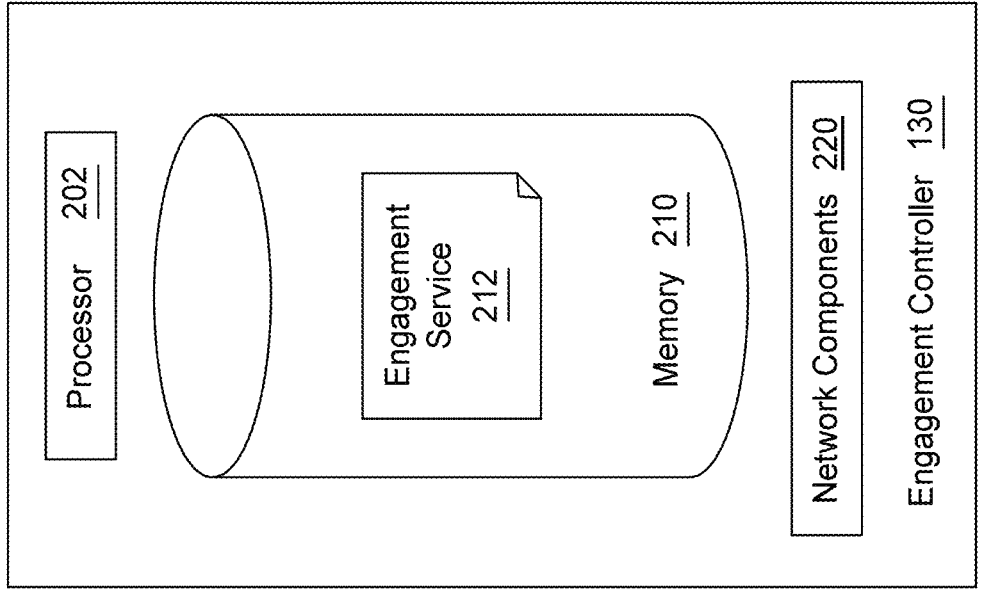

FIG. 2 depicts a block diagram for an engagement controller 130 and a resupply engine 140 to interact with an automated resupply engine, according to one embodiment. The engagement controller 130 includes a processor 202, a memory 210, and network components 220. The memory 210 may take the form of any non-transitory computer-readable medium. The processor 202 generally retrieves and executes programming instructions stored in the memory 210. The processor 202 is representative of a single central processing unit (CPU), multiple CPUs, a single CPU having multiple processing cores, graphics processing units (GPUs) having multiple execution paths, and the like.

The network components 220 include the components necessary for the engagement controller 130 to interface with a suitable communication network (e.g., a communication network interconnecting various components of the computing environment 100 illustrated in FIG. 1, or interconnecting the computing environment 100 with other computing systems). For example, the network components 220 can include wired, WiFi, or cellular network interface components and associated software. Although the memory 210 is shown as a single entity, the memory 210 may include one or more memory devices having blocks of memory associated with physical addresses, such as random access memory (RAM), read only memory (ROM), flash memory, or other types of volatile and/or non-volatile memory.

The memory 210 generally includes program code for performing various functions related to use of the engagement controller 130. The program code is generally described as various functional "applications" or "modules" within the memory 210, although alternate implementations may have different functions and/or combinations of functions. Within the memory 210, the engagement service 212 facilitates patient and physician engagement for automated medical resupply (e.g., using the patient engagement layer 110 and physician engagement layer 120 illustrated in FIG. 1). This is discussed further, below, with regard to FIGS. 3-9.

The resupply engine 140 includes a processor 252, a memory 260, and network components 270. The memory 260 may take the form of any non-transitory computer-readable medium. The processor 252 generally retrieves and executes programming instructions stored in the memory 260. The processor 252 is representative of a single central processing unit (CPU), multiple CPUs, a single CPU having multiple processing cores, graphics processing units (GPUS) having multiple execution paths, and the like.

The network components 270 include the components necessary for the resupply engine 140 to interface with a suitable communication network (e.g., a communication network interconnecting various components of the computing environment 100 illustrated in FIG. 1, or interconnecting the computing environment 100 with other computing systems). For example, the network components 270 can include wired, WiFi, or cellular network interface components and associated software. Although the memory 260 is shown as a single entity, the memory 260 may include one or more memory devices having blocks of memory associated with physical addresses, such as random access memory (RAM), read only memory (ROM), flash memory, or other types of volatile and/or non-volatile memory.

The memory 260 generally includes program code for performing various functions related to use of the resupply engine 140. The program code is generally described as various functional "applications" or "modules" within the memory 260, although alternate implementations may have different functions and/or combinations of functions. Within the memory 260, the resupply engine 140 facilitates automated medical resupply. This is discussed further, below, with regard to FIGS. 3-8.

While the engagement controller 130 and resupply engine 140 are each illustrated as a single entity, in an embodiment, the various components can be implemented using any suitable combination of physical compute systems, cloud compute nodes and storage locations, or any other suitable implementation. For example, the engagement controller 130, the resupply engine 140, or both, could be implemented using a server or cluster of servers. As another example, the engagement controller 130, the resupply engine 140, or both, can be implemented using a combination of compute nodes and storage locations in a suitable cloud environment. For example, one or more of the components of the engagement controller 130, the resupply engine 140, or both, can be implemented using a public cloud, a private cloud, a hybrid cloud, or any other suitable implementation.

Although FIG. 2 depicts the engagement service 212 and the resupply service 262 as being separately located in respective memories 210 and 260, that representation is also merely provided as an illustration for clarity. More generally, the engagement controller 130, the resupply engine 140, or both, may include one or more computing platforms, such as computer servers for example, which may be co-located, or may form an interactively linked but distributed system, such as a cloud-based system, for instance. As a result, the processors 202 and 252, and the memories 210 and 260, may correspond to distributed processor and memory resources within the computing environment 100. Thus, it is to be understood that any, or all, of the engagement service 212 and the resupply service may be stored together, or remotely from one another, within the distributed memory resources of the computing environment 100.

Figure 3:
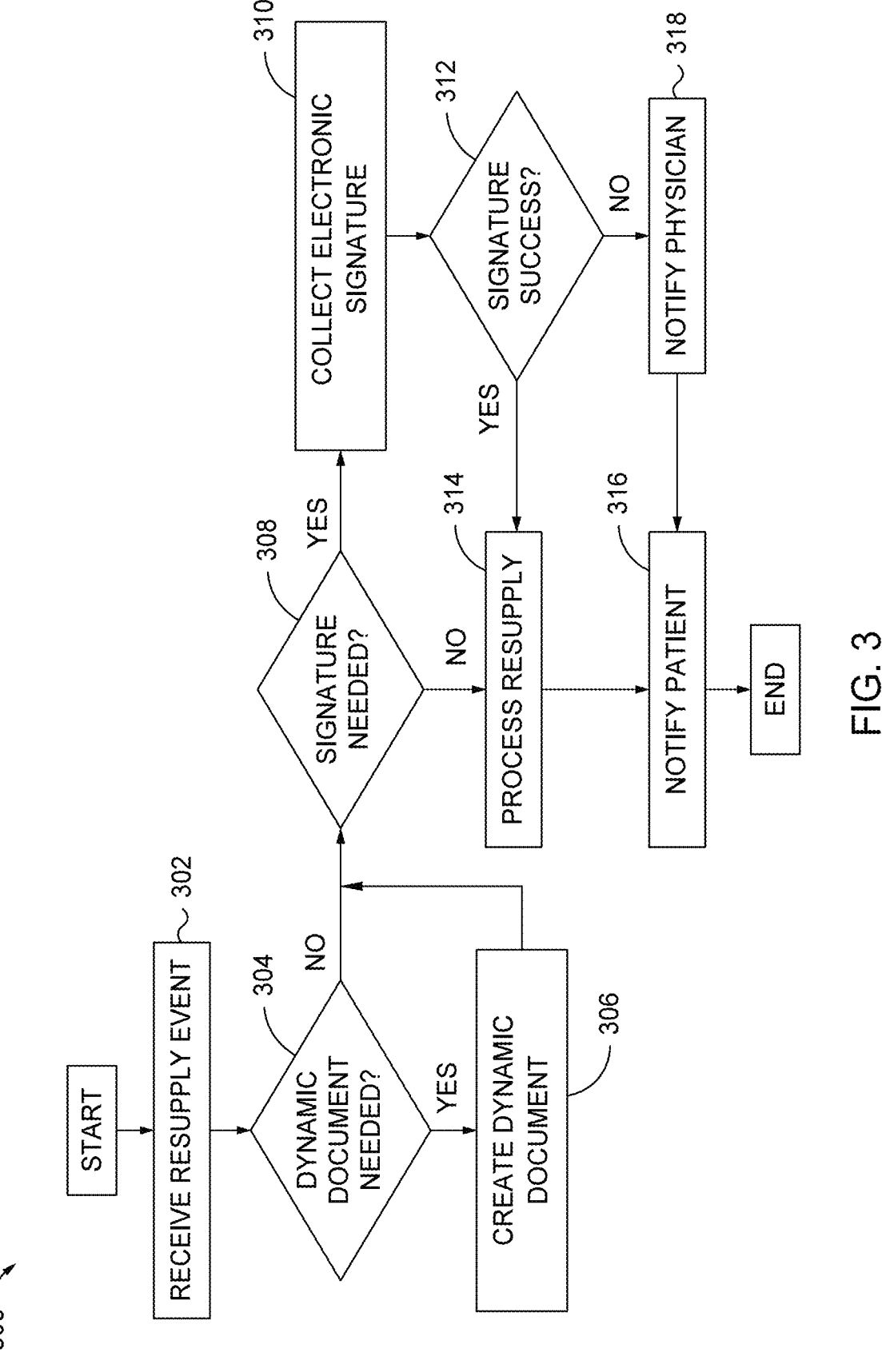
FIG. 3 is a flowchart illustrating an automated medical resupply engine, according to one embodiment.

FIG. 3 is a flowchart 300 illustrating an automated medical resupply engine, according to one embodiment. At block 302 a resupply service (e.g., the resupply service 262 illustrated in FIG. 2) receives a resupply event. For example, the resupply service can receive an event describing an upcoming resupply for a patient. In an embodiment, the resupply event is generated by a resupply engine (e.g., the resupply engine 140 illustrated in FIGS. 1-2) or by another suitable software system. For example, the resupply engine can track necessary resupplies for patients, and can trigger events, as necessary, to initiate a resupply. In this example, the resupply engine can analyze policy rules (e.g., insurance policy rules, medical care policy rules, and any other suitable policy rules) to identify the appropriate time to trigger a resupply event. In an embodiment the resupply engine can further review prior resupply orders (e.g., for a given patient, category of patients, or group of patients) to identify the appropriate time to trigger a resupply event. The resupply engine can review prior orders instead of, or in addition to, reviewing policy rules.

Alternatively, or in addition, the resupply event is generated by an engagement service (e.g., the engagement service 212 illustrated in FIG. 2). For example, a patient can initiate an electronic message from a patient computing device (e.g., as part of the patient engagement layer 110) describing a resupply order. The engagement service can generate a resupply event from this message and provide the resupply event to the resupply engine. This message can be initiated by a patient, can come in response to a prompt or reminder to the patient (e.g., an SMS message or another electronic message reminding the patient to resupply HME), or can come from any other source.

In an embodiment, the resupply order includes identifying information used to fulfill the order. For example, the resupply order can include a referral ID or any other suitable identifier. The resupply service, or another suitable service, can use the referral ID to identify the resupply request. For example, the resupply service can query an electronic repository (e.g., an electronic database, cloud storage repository, or any other suitable electronic repository) using the referral ID. This is merely an example, and the resupply order can include any suitable identifying information.

At block 304, the resupply service (or another suitable service) determines whether dynamic documents are needed. For example, the resupply service can determine that the resupply order relates to a prescription item. The resupply service can generate a dynamic electronic document that contains information about the patient, the approving physician, and the resupply event (e.g., the resupply request). The engagement service can then provide this electronic document to the physician, and can facilitate having the physician sign the document to fulfill the resupply request.

If the resupply service determines that a dynamic document is needed, the flow proceeds to block 306. At block 306, the resupply service creates the dynamic document. For example, as discussed above, the resupply service can generate a dynamic electronic document that contains information about the patient, the approving physician, and the resupply event (e.g., the resupply request). The dynamic electronic document can further include a document identifier (e.g., a unique identifier within the engagement and resupply system). This is discussed further, below, with regard to FIGS. 4-6.

At block 308, the resupply service determines whether a signature is needed. For example, as discussed above, the resupply order may relate to a prescription item that requires a physician signature. If it does, the flow proceeds to block 310.

At block 310, the engagement service collects the electronic signature. For example, the engagement system can provide the dynamic document created at block 306 to a physician engagement layer (e.g., the physician engagement layer 120 illustrated in FIG. 1) and can request a signature. The physician engagement layer can collect the signature. Further, as discussed above in relation to FIG. 1, the engagement service can determine whether the physician engagement layer is compatible with the engagement service. In an embodiment, the engagement service proceeds to collect the electronic signature only if the physician engagement service is compatible. Collecting the electronic signature is discussed further, below, with regard to FIGS. 7-9.

At block 312, the engagement service determines whether the signature collection was a success. For example, the physician engagement layer can determine that the signature was successful or unsuccessful, and can provide an electronic message notifying the engagement service. This is discussed further, below, with regard to FIGS. 8A-C.

If collecting the electronic signature is successful, the flow proceeds to block 314. At block 314 the resupply service processes the resupply. For example, the resupply service can complete the order (e.g., using a suitable logistics system), can handle billing and payment, and can request delivery to the patient.

At block 316, the engagement service notifies the patient. For example, the engagement service can use the patient engagement layer to notify the patient that the resupply order was processed successfully, using a suitable electronic message. Further, as discussed above in relation to FIG. 1, the engagement service can determine whether the patient engagement layer is compatible with the engagement service. In an embodiment, the engagement service proceeds to notify the patient only if the patient engagement service is compatible.

Returning to block 312, if the electronic signature is not successful, the flow proceeds to block 318. At block 318 the engagement service notifies the physician that the signature was not successful. For example, the engagement service can transmit an electronic message to the physician indicating that the signature was not successful. This is merely an example, and the engagement service can use a telephone call or any other notification. In an embodiment, the physician notification requests that the physician complete the necessary signatures and documentation to complete the resupply. Further, at block 316 the engagement service can notify the patient that the resupply was not successful (e.g., because of the signature failure). This is discussed further with regard to FIG. 8C, below.

Figure 4:
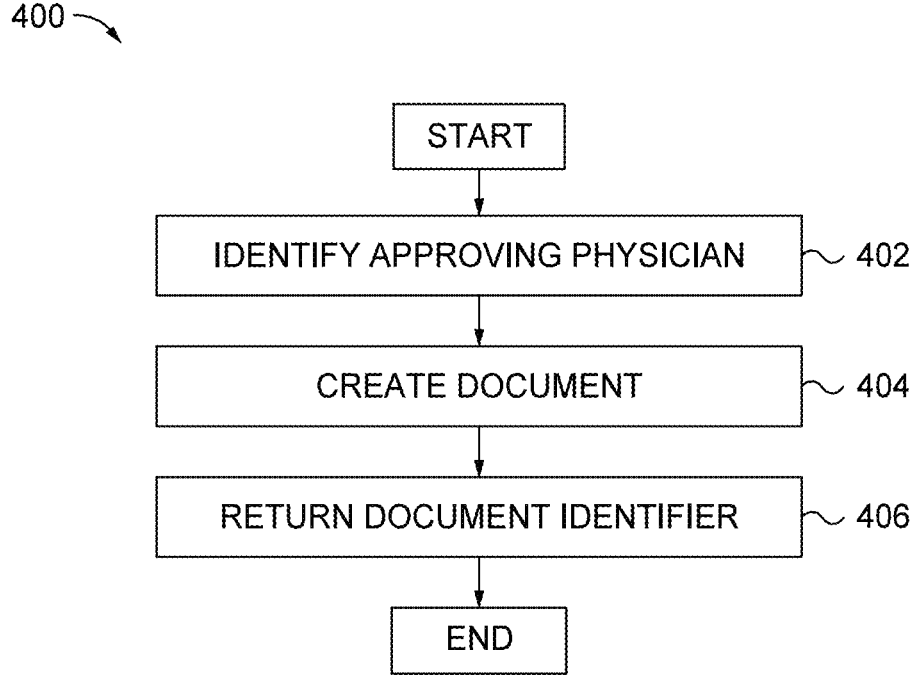
FIG. 4 is a flowchart illustrating dynamic document creation for an automated medical resupply engine, according to one embodiment.

FIG. 4 is a flowchart 400 illustrating dynamic document creation for an automated medical resupply engine, according to one embodiment. In an embodiment, FIG. 4 relates to block 306 illustrated in FIG. 3. At block 402 a resupply service (e.g., the resupply service 262 illustrated in FIG. 2) identifies the approving physician. For example, as discussed above, in an embodiment the dynamic document is created to facilitate review of a prescription by an approving physician. The resupply service can use a referral ID, or any other suitable identifier associated with the resupply request, to identify the approving physician. For example, the resupply service can look up the approving physician in a suitable electronic repository (e.g., an electronic database) using the referral ID. As another example, the resupply service can use a third party prescription system (e.g., using a suitable API) to identify the approving physician. These are merely examples, and the resupply service can use any suitable technique.

Further, in an embodiment, an engagement service (e.g., the engagement service 212 illustrated in FIG. 2) determines how to contact the physician by identifying an electronic healthcare system with which the physician is associated. For example, as discussed above in relation to FIG. 1, the engagement service can query multiple electronic healthcare systems using a suitable identifier associated with the physician (e.g., an NPI) to identify which electronic healthcare system is currently associated with the physician. This is discussed further, below, with regard to FIG. 5. Further, as discussed above in relation to FIG. 1, the engagement service can determine whether the electronic healthcare system with which the physician is associated is compatible with the engagement service. In an embodiment, the engagement service only if the electronic healthcare system with which the physician is associated is compatible.

At block 404, the resupply service creates the dynamic document. For example, the resupply service can create a document identifying the patient, the approving physician, and the resupply event (e.g., the resupply request). This is discussed further, below, with regard to FIG. 6. As another example, the resupply service can provide the patient, approving physician, and resupply event information to an engagement service (e.g., the engagement service 212 illustrated in FIG. 2) and the engagement service can create the document.

At block 406, the resupply service returns a document identifier. In an embodiment, the resupply service (or other suitable service) creates a document identify associated with the dynamically created document. This document identifier can be unique within the resupply engine (e.g., within the resupply engine 140 illustrated in FIGS. 1-2) and the engagement controller (e.g., within the engagement controller 130 illustrated in FIGS. 1-2) and can be used to uniquely identify the newly created document. The resupply service can return the document identifier to the entity requesting creation of the document (e.g., the engagement controller).

Figure 5:
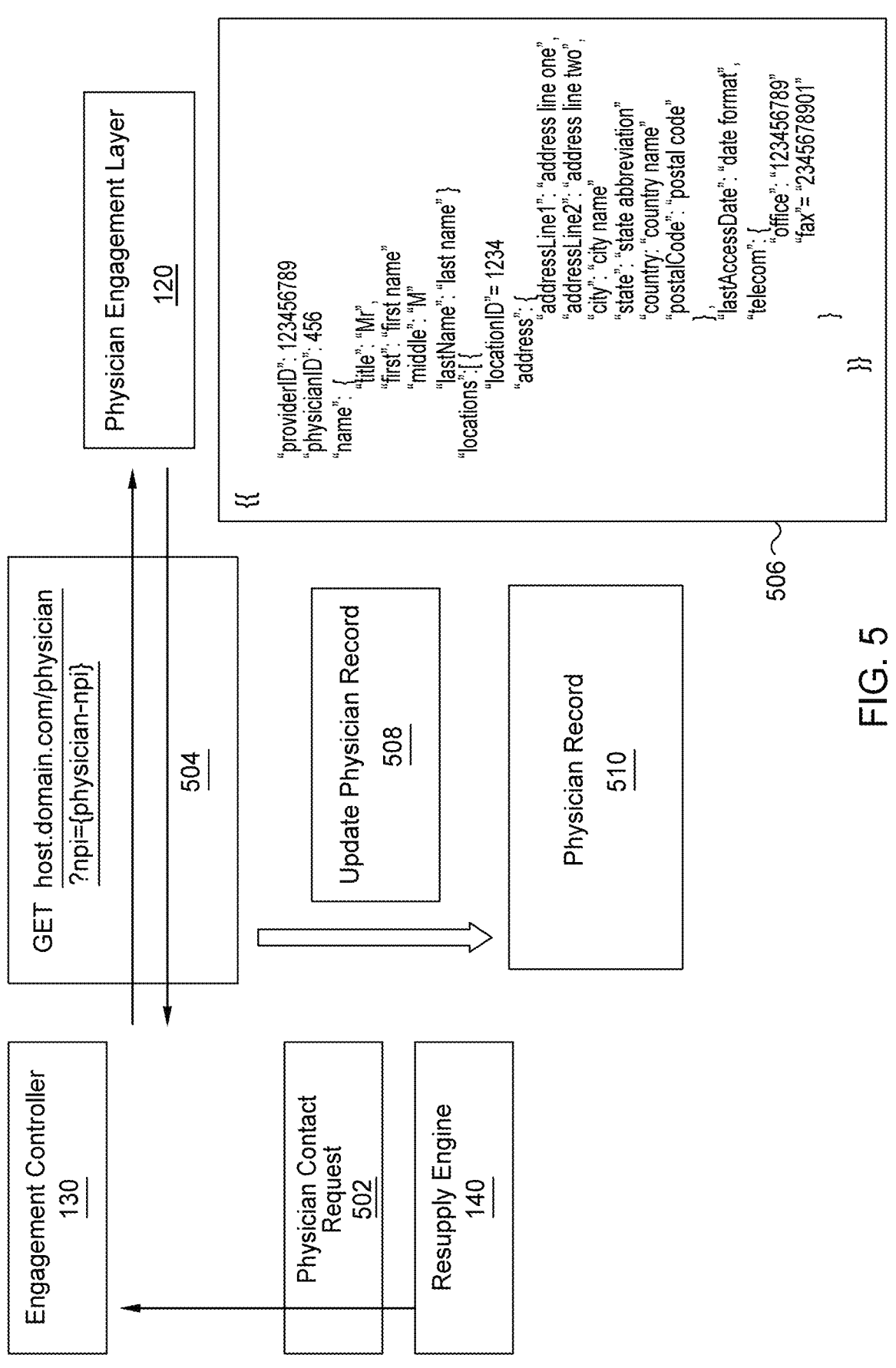
FIG. 5 illustrates identifying an approving physician for dynamic document creation for an automated medical resupply engine, according to one embodiment.

FIG. 5 illustrates identifying an approving physician for dynamic document creation for an automated medical resupply engine, according to one embodiment. In an embodiment, FIG. 5 corresponds with block 402 discussed above in relation to FIG. 4. A resupply engine 140 (e.g., the resupply service 262 illustrated in FIG. 2) transmits a physician contact request 502 to an engagement controller 130 (e.g., the engagement service 212 illustrated in FIG. 2). For example, the resupply engine 140 can include an identifier for the physician (e.g., an NPI), an identifier for a healthcare entity with which the physician is associated (if available), and any other suitable information in the physician contact request 502.

In an embodiment, the engagement controller transmits an API request 504 to a physician engagement layer 120. In one embodiment, the engagement controller identifies a healthcare entity with which the physician is associated (e.g., among a number of available healthcare entities) using a healthcare entity identifier provided by the resupply engine 140. Alternatively, or in addition, as discussed above in relation to FIG. 1 the engagement controller identifies a healthcare entity with which the physician is associated by transmitting queries to each potential electronic healthcare system and waiting for a success response from one of the electronic healthcare systems. Further, as discussed above in relation to FIG. 1, the engagement service can determine whether the physician engagement layer is compatible with the engagement service. In an embodiment, the engagement service proceeds to collect the electronic signature only if the physician engagement service is compatible.

In an embodiment, the physician engagement layer 120 responds to the API request 504 with physician information 506. For example, the physician information 506 can include information relating to the physician, including an identifier for a location at which the physician can be contacted. In an embodiment, a given physician can practice at multiple locations, and the physician information 506 can identify all the available locations.

In an embodiment, the engagement controller 130 receives the physician information 506, and transmits an update physician record 508 message to update a physician record 510. For example, the engagement controller 130 can update a physician record 510 stored in a repository accessible to the engagement controller 130, the resupply engine 140, or both, to reflect the physician information 506. In an embodiment the physician record 510 can be stored in a local storage location, or a remote storage location, including a suitable cloud storage location. Further, the physician record 510 can be stored in a suitable electronic database (e.g., a relational database or a graph database) or any other suitable repository.

Further, in an embodiment, the engagement controller 130 can update an enrolled status for the physician in the physician record 510, to indicate that the physician is accessible (e.g., for electronic signature). In an embodiment, the engagement service can also determine whether the physician is currently active. For example, the engagement service can identify a last signature date for a given physician. If the last signature date is sufficiently recent (e.g., occurred within a threshold period in the past), the physician is considered active. If the last signature date is not sufficiently recent (e.g., occurred outside of a threshold period in the past), the physician is considered likely inactive and the enrolled status is not updated.

Figure 6:
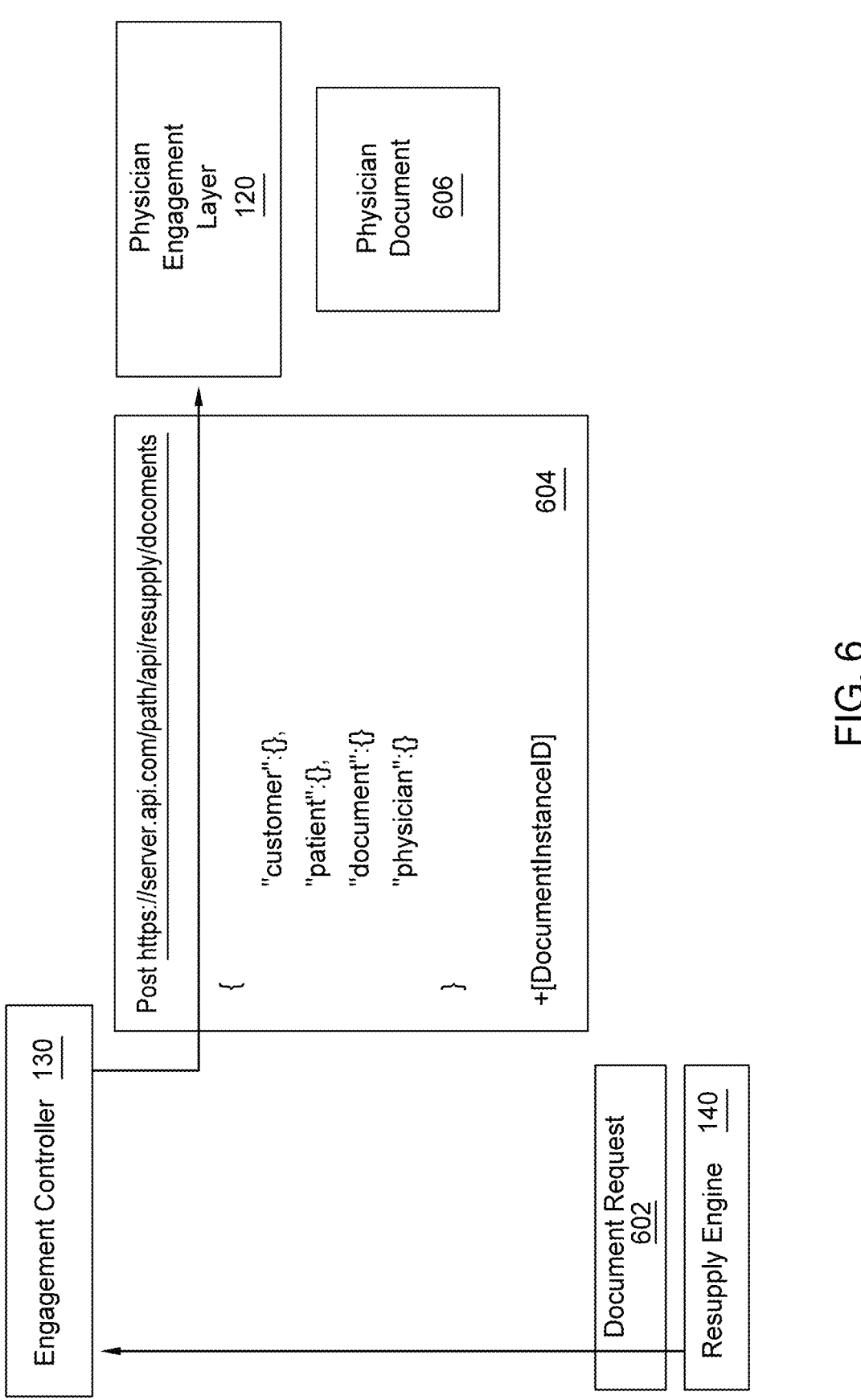
FIG. 6 further illustrates dynamic document creation for an automated medical resupply engine, according to one embodiment.

FIG. 6 further illustrates dynamic document creation for an automated medical resupply engine, according to one embodiment. In an embodiment, FIG. 6 provides additional description for creating a dynamic document, as discussed above in relation to block 306 illustrated in FIG. 3 and in FIG. 4. A resupply engine 140 transmits a document request 602 to an engagement controller 130. As discussed above, in an embodiment the document request 602 includes identifying information for the patient, the approving physician, and resupply event (e.g., the resupply request).

The engagement controller 130 transmits an API call 604 to a physician engagement layer 120. For example, the engagement controller 130 can make a call to the API at https://server.api.com/path/api/resupply/documents with information for a customer (e.g., a healthcare entity facilitating resupply), a patient (e.g., the patient being resupplied), a document (e.g., the document being created), and a physician (e.g., the approving physician). These are merely examples, and the API call 604 can include any suitable information (e.g., diagnosis codes, length of service information, product information, or any other suitable information).

The physician engagement layer 120 can use the API call 604 to create an electronic document 606, suitable for a physician to review and sign (if appropriate) to fulfil a prescription. As discussed above, in one embodiment the physician engagement layer creates the document using information from the engagement controller 130, resupply engine 140, or both. Alternatively, or in addition, the engagement controller 130 creates the document, or the resupply engine 140 creates the document.

Figure 7:
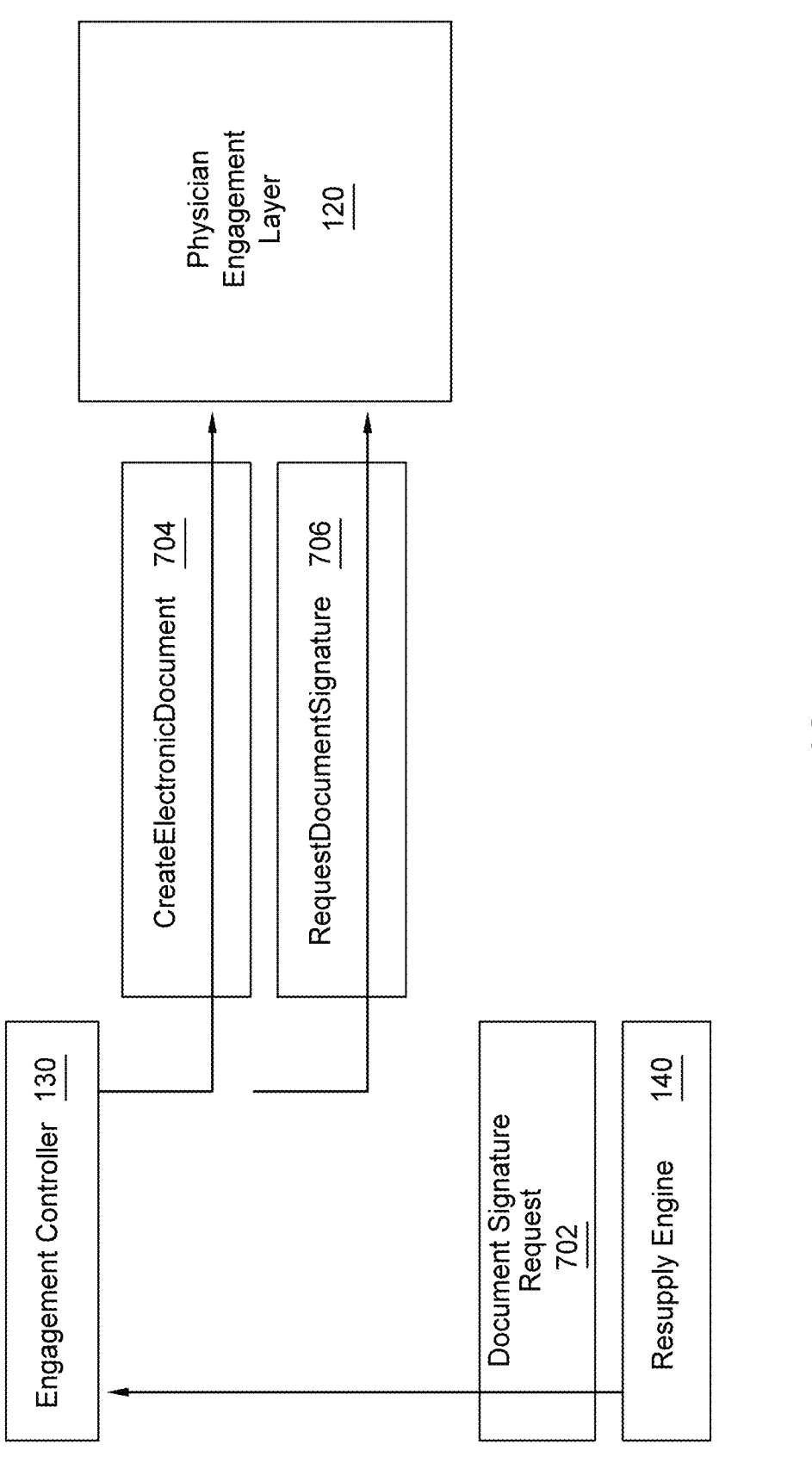
FIG. 7 illustrates an electronic signature application programming interface (API) for an automated medical resupply engine, according to one embodiment.
Figure 8A:
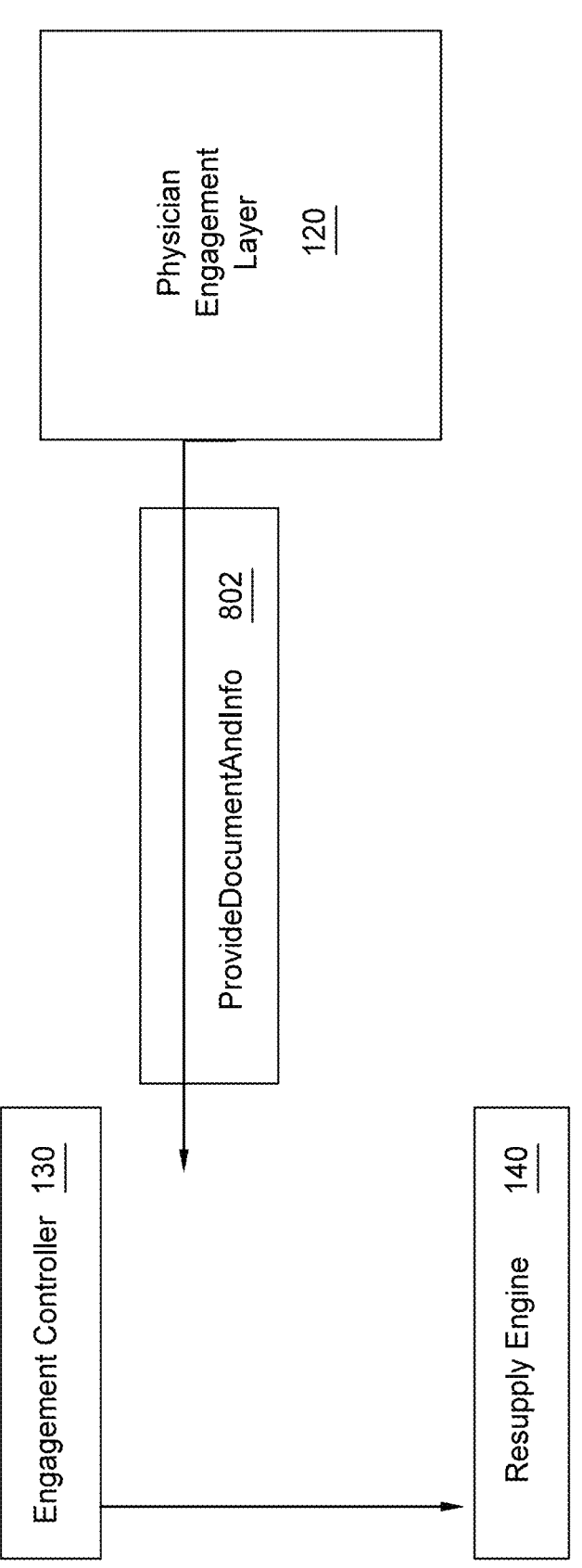
FIGS. 8A-C further illustrates an electronic signature API for an automated medical resupply engine, according to one embodiment.
Figure 8B:
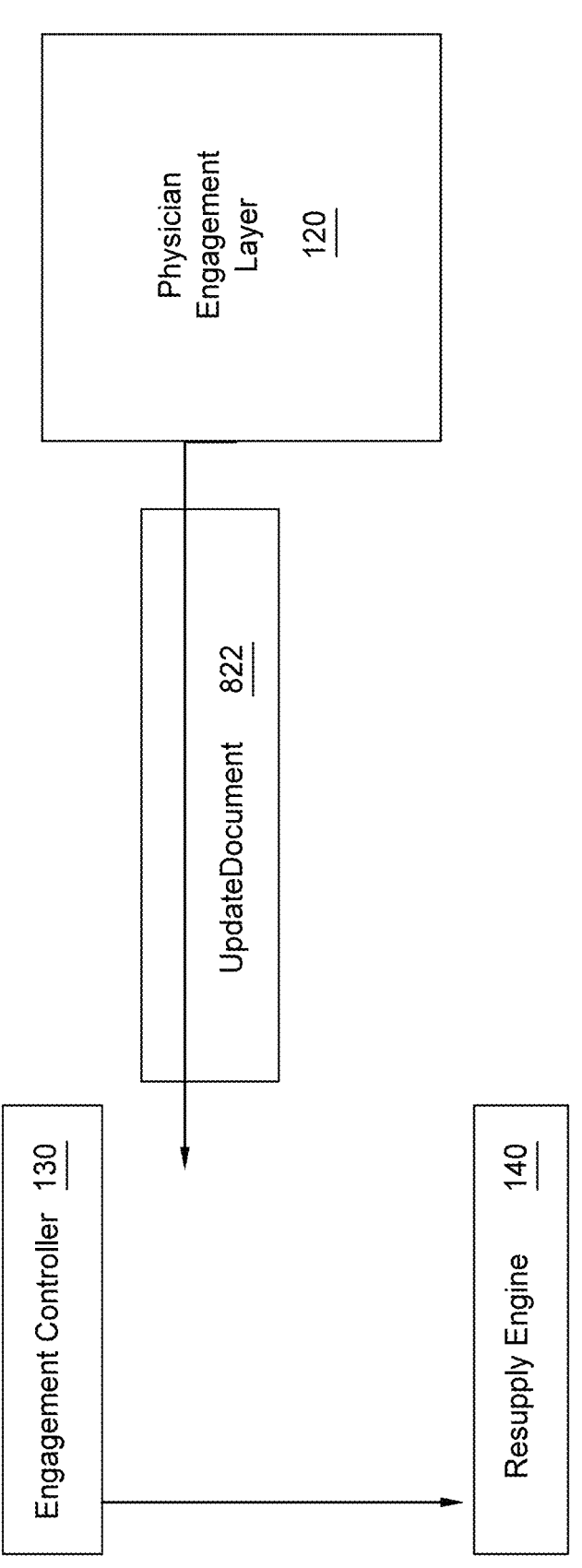
Figure 8C:
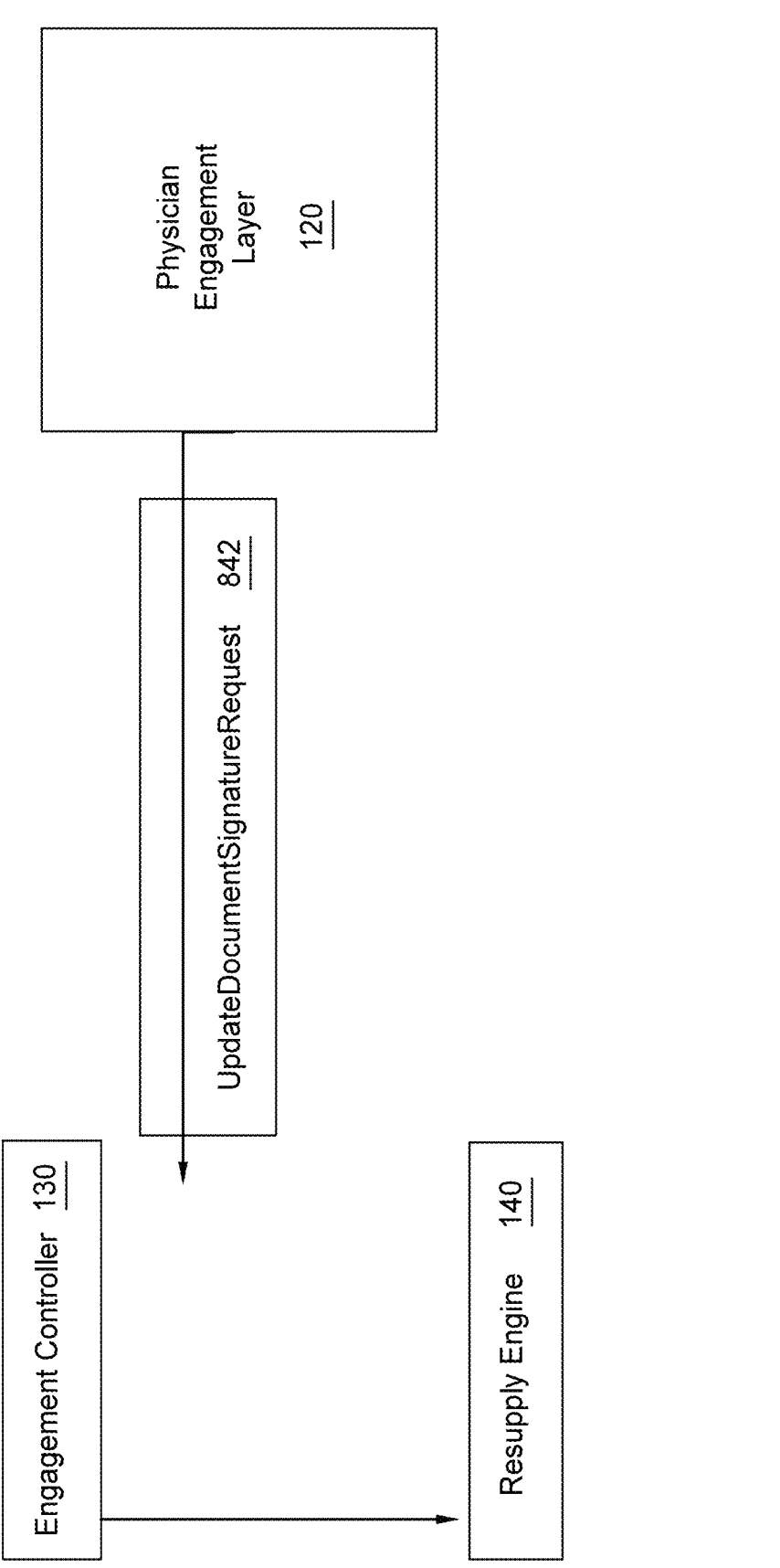

FIG. 7 illustrates an electronic signature API for an automated medical resupply engine, according to one embodiment. In an embodiment, FIG. 7 illustrates API calls from an engagement controller 130 to a physician engagement layer 120. FIGS. 8A-C, discussed further below, illustrates API calls from the physician engagement layer 120 to the engagement controller 130.

A resupply engine 140 transmits a document signature request 702 to an engagement controller 130. In an embodiment the document signature request 702 is an example of a document request 502, illustrated in FIG. 5. The document signature request 702 includes identifying information for the patient, the approving physician, and resupply event (e.g., the resupply request).

In an embodiment, the engagement controller 130 responds to the document signature request 702 by issuing a create electronic document API call 704 to the physician engagement layer 120, and a request document signature API call 706. For example, the create electronic document API call 704 can correspond to the API call 604 illustrated in FIG. 6. The create electronic document API call 704 can include information for a customer (e.g., a healthcare entity facilitating resupply), a patient (e.g., the patient being resupplied), a document (e.g., the document being created), and a physician (e.g., the approving physician). Further, in an embodiment, the physician engagement layer 120 responds to the create electronic document API call 704 with an identifier for the newly created document (e.g., a unique identifier).

In an embodiment, the request document signature API call 706 notifies the physician engagement layer 120 that a document (e.g., the document created with the API call 704) is available for review and signature for a physician. In an embodiment, the request document signature API call 706 includes the document ID (e.g., the unique document ID) returned in response to the API call 704. The physician engagement layer 120 can use the document ID to identify the document for signature by a physician.

FIGS. 8A-C further illustrate an electronic signature API for an automated medical resupply engine, according to one embodiment. Starting with FIG. 8A, in an embodiment, the physician engagement layer 120 makes a provide document and information API call 802 to the engagement controller 130. The provide document and information API call 802 provides a copy of the signed document (e.g., a PDF copy of the signed document) for the engagement controller 130 to store in an electronic repository, assuming the signature request (e.g., the request document signature API call 706 illustrated in FIG. 7). In an embodiment, the provide document and information API call 802 further provides data elements describing the signed document. This allows the engagement controller 130, the resupply engine 140, or both, to identify the characteristics of the signed document without parsing a PDF document. The engagement controller 130, the resupply engine 140, or both, can use the provided data elements to complete the resupply, and can notify the patient that the resupply was successful.

In an embodiment, portions of a document signature can be approved while other portions are not approved. For example, a request document signature API call 706, as illustrated in FIG. 7, can include multiple elements requiring approval. The provide document and information API call 802 (or another suitable API call as illustrated in FIGS. 8B-C) can indicate approval for some elements and no approval for other elements. The engagement controller 130, the resupply engine 140, or both, can then use that partial approval to complete the approved aspects of the resupply, and notify the patient of the status.

Turning to FIG. 8B, in an embodiment the physician engagement layer 120 can further make an update document API call 822 to the engagement controller 130. The update document API call 822 can update a document previously stored in a repository associated with the engagement controller 130 (e.g., stored using the API call 802). For example, the update document API call 822 can notify the engagement controller that a document has been signed, or can update any other suitable aspect of the document (e.g., a stored document).

Moving to FIG. 8C, in an embodiment the physician engagement layer 120 can further make an update document signature request API call 842 to the engagement controller 130. For example, the update document signature request API call 842 can be used to indicate that the physician engagement layer 120 has rejected a signature request, or a portion of a signature request. For example, a physician may reject a prescription request. The update document signature request API call 842 can be used to indicate this rejection, so that the engagement controller can notify the patient. As another example, an error may occur in the document signature request (e.g., the document cannot be found or cannot be created correctly, the physician cannot be found, the physician system does not support electronic signatures, or any other suitable error). The update document signature request API call 842 can be used to indicate the error.

In an embodiment, the update document signature request API call 842 can indicate a reason for the rejection or error. For example, the physician could indicate that the relevant patient is not in that physician's care, could indicate that the patient must be examined before the request can be approved, or can indicate any other suitable reason. In an embodiment, the engagement controller 130 can provide this information to a patient engagement layer (e.g., the patient engagement layer 110 illustrated in FIG. 1), and the patient engagement layer can use the reason for failure to provide appropriate notification to the patient.

In an embodiment, the update document signature request API call 842 can indicate the error using a suitable code or pre-determined value. Alternatively, the update document signature request API call 842 can return a textual indication of the reason for failure (e.g., a textual explanation provided by the physician). In an embodiment, the engagement controller 130 can parse this textual indication to identify the cause of the failure. For example, the engagement controller 130 can use a suitable machine learning (ML) model to perform natural language processing (NLP) on the textual indication. The engagement controller 130 can use NLP to identify the meaning of the textual indication, and to provide appropriate engagement with the patient (e.g., a suitable indication of the reason for failure).

Figure 9:
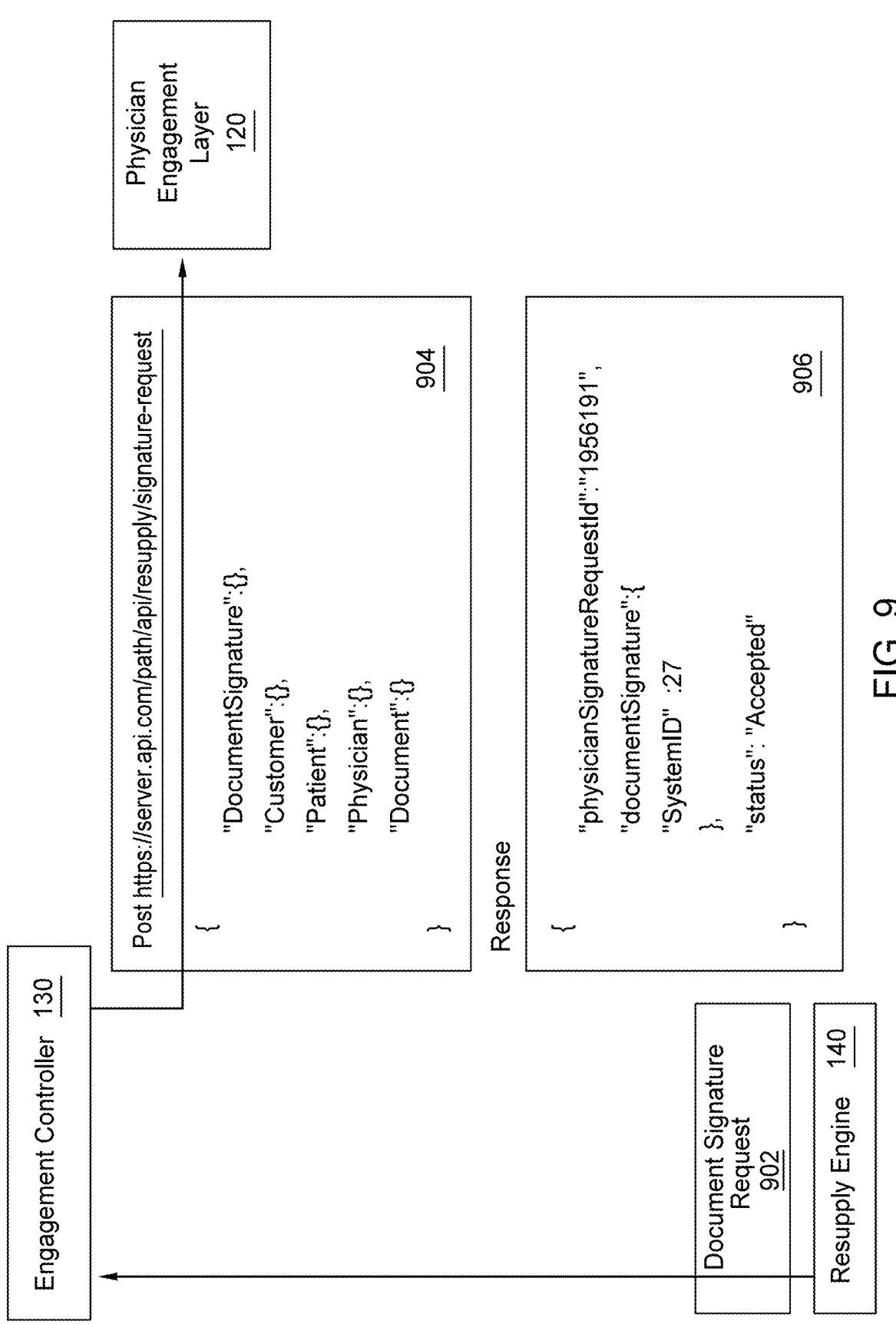
FIG. 9 illustrates requesting a care provider signature for an automated medical resupply engine, according to one embodiment.

FIG. 9 illustrates requesting a care provider signature for an automated medical resupply engine, according to one embodiment. In an embodiment, FIG. 9 further illustrates the flow discussed above with regard to FIGS. 7-8C. A resupply engine 140 transmits a document signature request 902 to an engagement controller 130. In an embodiment the document signature request 902 corresponds to the document signature request 602 illustrated in FIG. 6, and includes identifying information for the patient, the approving physician, and resupply event (e.g., the resupply request).

The engagement controller 130 transmits an API call 904 to a physician engagement layer 120. For example, the API call 904 can correspond to the create electronic document API call 704 illustrated in relation to FIG. 7. The engagement controller 130 can make a call to the API at https://server.api.com/path/api/resupply/documents with information for a customer (e.g., a healthcare entity facilitating resupply), a patient (e.g., the patient being resupplied), a document (e.g., the document being created), and a physician (e.g., the approving physician), requesting that the physician engagement layer 120 creates the document. As noted above, this is merely an example, and the engagement controller 130, resupply engine 140, or both, can create the document.

In an embodiment, the API call 904 further corresponds to the request document signature API call 706 illustrated in FIG. 7. The API call 904 notifies the physician engagement layer 120 that the created document is available for review and signature for a physician. In an embodiment, the API call 904 includes the document ID (e.g., the unique document ID) returned in response to the API call 704. The physician engagement layer 120 can use the document ID to identify the document for signature by a physician.

In an embodiment, the physician engagement layer 120 responds with a response 906. The response 906 includes an identifier for the signature request (e.g., a unique identifier), and a system identifier. In an embodiment, the response 906 further includes a status.

Figure 10:
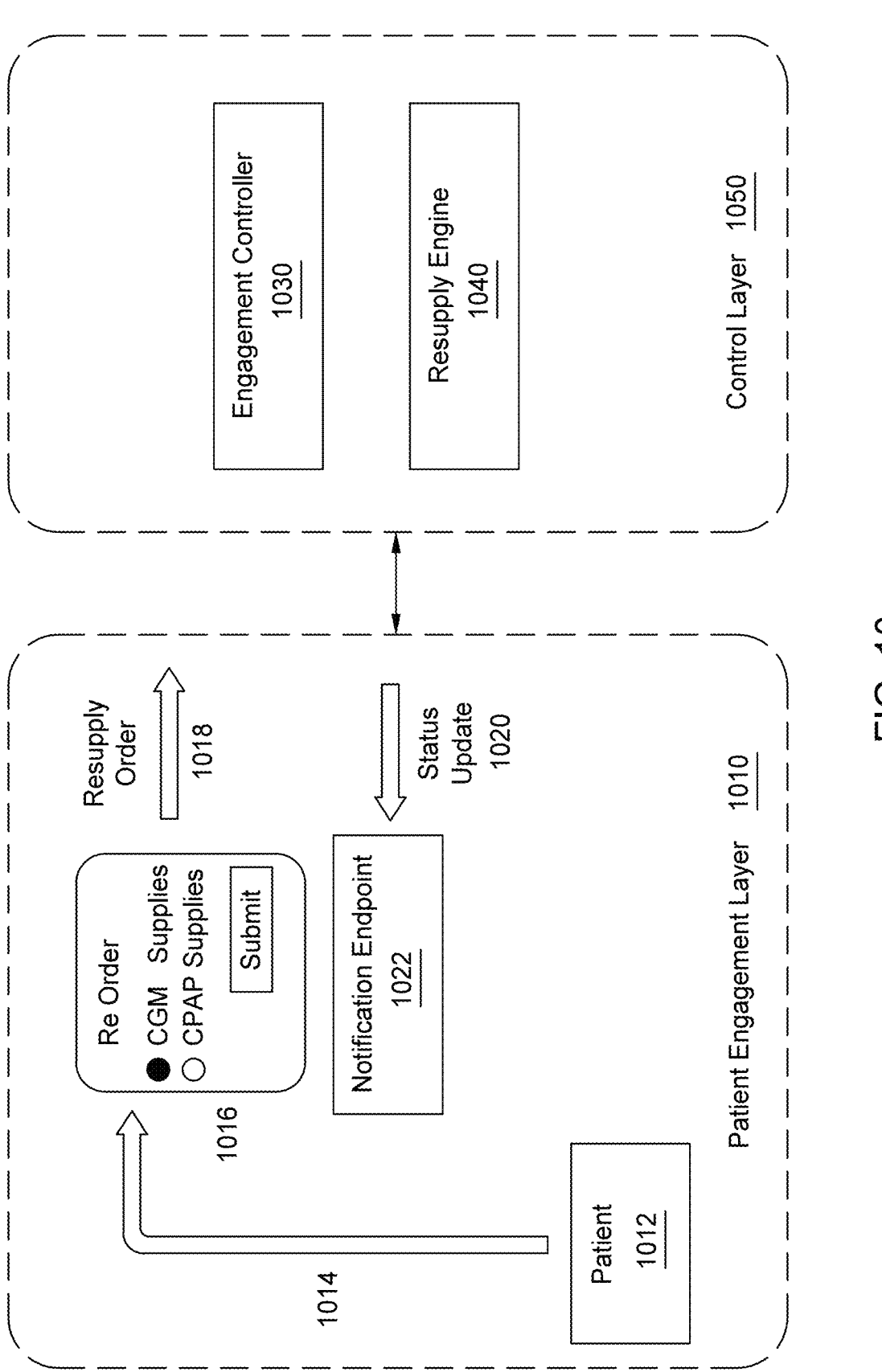
FIG. 10 illustrates patient engagement for an automated medical resupply engine, according to one embodiment.

FIG. 10 illustrates patient engagement for an automated medical resupply engine, according to one embodiment. In an embodiment, a patient engagement layer 1010 (e.g., the patient engagement layer 110 illustrated in FIG. 1) relates to a patient 1012. The patient 1012 makes a request 1014 to a patient device 1016. In an embodiment, the patient device 1016 can be any suitable electronic or computing device, including a smartphone, a tablet, a laptop computer, a desktop computer, a wearable device, a medical device, an Internet of Things (IoT) device, or any other suitable device. In an embodiment, the request 1014 is a resupply request, and the patient device 1016 includes a suitable user interface reflecting the request. The patient 1012 can use the user interface to initiate the request 1014, to cancel the request

1014, to modify the request 1014, to monitor the status of the request 1014, or for any other suitable use.

In an embodiment, the patient device 1016 transmits a resupply order 1018 to a control layer 1050 (e.g., the control layer 150 illustrated in FIG. 1). For example, the patient device 1016 can transmit a resupply order 1018 to an engagement controller 1030 (e.g., the engagement controller 130 illustrated in FIG. 1). As discussed above in relation to block 302 illustrated in FIG. 3, the engagement controller 1030 can receive this resupply order 1018 as a resupply event and can use the resupply order 1018 to trigger a resupply. The control layer 1050 is discussed further, below, with regard to FIG. 11.

In an embodiment, the control layer 150 provides a status update 1020 to the patient engagement layer 1010, which hits a notification endpoint 1022. For example, the engagement controller 1030, a resupply engine 1040 (e.g., the resupply engine 140 illustrated in FIG. 1), or both, can provide the status update 1020 to the patient engagement layer 1010. In an embodiment, the status update is 1020 is provided to the patient 1012 through the user interface of the patient device 1016. For example, the patient device 1016 can provide a message (e.g., an SMS message, MMS message, or any other suitable electronic message) or indication reflecting the status. This is merely an example, and the status update 1020 can be provided to the patient 1012 in any suitable fashion (e.g., a voice message or telephone call, a message on another electronic device, or using any other suitable technique).

In an embodiment, the status update 1020 is merely one example of engagement from the control layer 1050 (e.g., from the engagement controller 1030) to the patient engagement layer 1010. For example, the engagement controller 1030 could also provide notification to the patient 1012, using the patient engagement layer, to suggest that the patient initiate a resupply order. As another example, the engagement controller 1030 could also provide notification to the patient 1012, using the patient engagement layer, when the patient may be at risk for prematurely discontinuing treatment, and a resupply could keep the patient engaged in treatment for longer.

In an embodiment, the engagement controller 1030 can initiate engagement with the patient engagement layer 1010 using a wide variety of patient data. This can include patient demographic data, patient contact information, patient payment details (e.g., credit card details), patient insurance details, social determinants of health (SDoH) data, medical device data, prior or pending resupply order data (e.g., for the subject patient, other patients, or both), and any other suitable data. In an embodiment, the engagement controller 1030 can use any aspect of this data to determine when to initiate patient engagement, and to assist in completing patient engagement (e.g., identifying how to contact the patient). In an embodiment, the engagement controller 1030 can determine whether the electronic healthcare system related to the patient engagement layer 1010 is compatible with the control layer 1050 (e.g., with the engagement controller 1030, the resupply engine 1040, or both). The engagement controller 1030 can decline to interact further with an incompatible patient engagement layer 1010.

Figure 11:
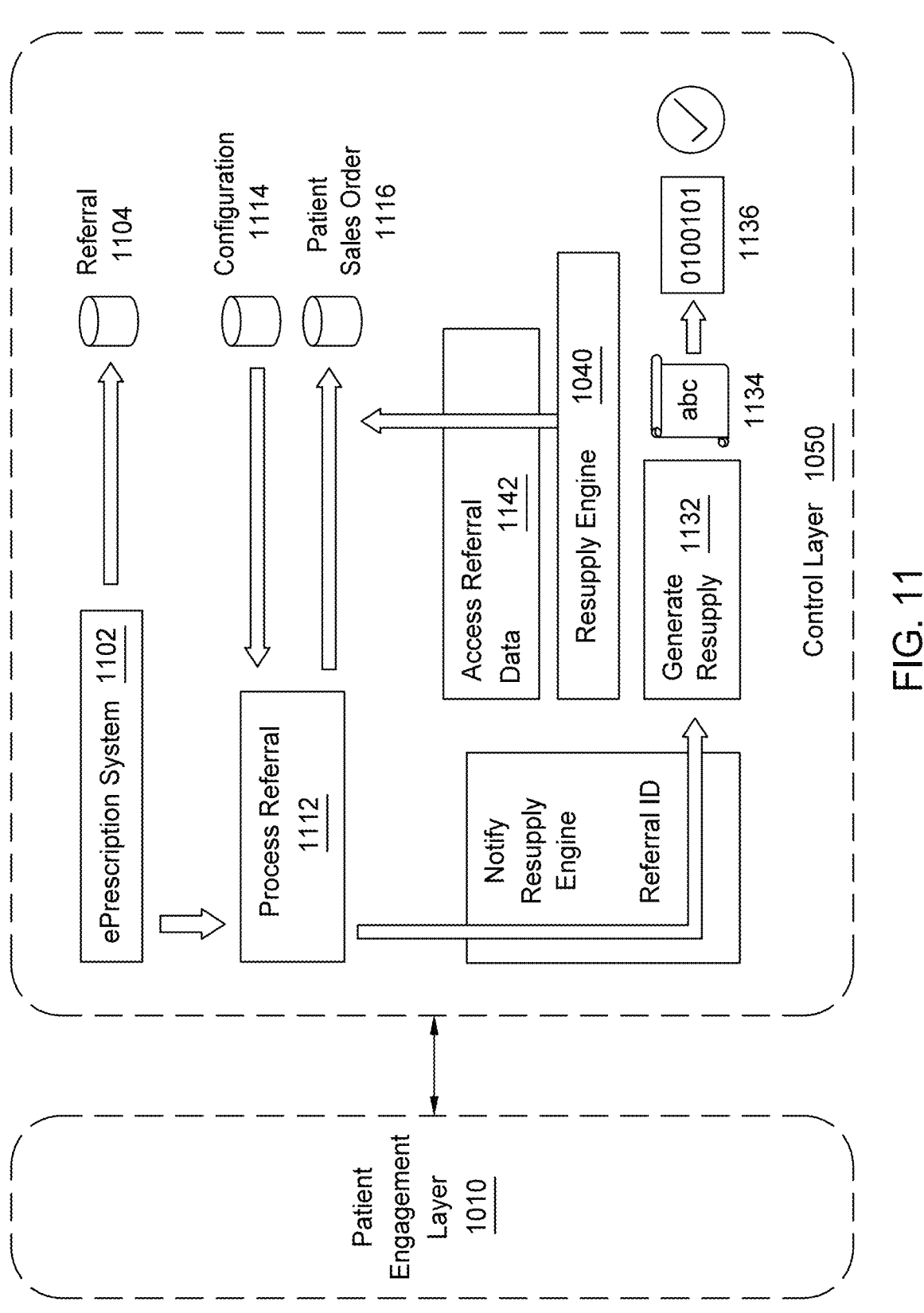
FIG. 11 further illustrates patient engagement for an automated medical resupply engine, according to one embodiment.

FIG. 11 further illustrates patient engagement for an automated medical resupply engine, according to one embodiment. In an embodiment, FIG. 11 corresponds with FIG. 10 and provides additional detail relating to the control layer 1050. For example, as discussed above in relation to FIG. 10, a resupply event can be initiated by a resupply order

1018 from a patient 1012. Alternatively, a resupply engine 1040, an ePrescription system 1102, or both, can initiate a resupply event.

In an embodiment, the resupply engine 1040 can access referral data 1142. The resupply engine 1040 can process the referral at block 1112, and can use configuration data 1114 to generate a patient sales order 1116. The ePrescription system 1102 can use referral data 1104 to process a referral at block 1112. In an embodiment, processing the referral at block 1112 further serves to notify the resupply engine 1040 and provide a referral ID, and to generate a resupply event. For example, as discussed above in relation to block 302 illustrated in FIG. 3, a resupply event can be generated by the resupply engine 1040 based on analyzing policy rules, reviewing prior resupply orders, or analyzing any other suitable information. The resupply engine 1040 can generate this resupply event at block 1132. In an embodiment, the resupply event 1132 can be used to generate a resupply request 1134, which can result in a success indication 1136 (assuming the resupply request 1134 is successful).

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in FIGS., those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112 (f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A computer-implemented method, comprising:
generating an event relating to resupply of one or more medical items for a patient, wherein the resupply requires approval from a physician;
transmitting, based on the event, a request for electronic approval of the resupply to an electronic healthcare system for the physician, comprising:
dynamically generating an electronic document relating to the required approval;
providing the electronic document to the electronic healthcare system for the physician, comprising transmitting an application programming interface (API) request for approval of the resupply; and
receiving an electronic message response from the electronic healthcare system for the physician indicating approval for the request, comprising receiving an API response indicating the approval, wherein the electronic healthcare system for the physician is compatible with the request for electronic approval of the resupply; and
initiating, based on the response, resupply of the one or more medical items, wherein the one or more medical items are used to treat the patient.

2. The computer-implemented method of claim 1, wherein transmitting the request for electronic approval of the resupply to the electronic healthcare system for the physician further comprises determining that the electronic healthcare system for the physician is compatible with the API request for approval of the resupply.

3. The computer-implemented method of claim 1, wherein the API response indicating the approval provides a signed electronic document and one or more electronic data elements describing the approval, the method further comprising:
analyzing the one or more electronic data elements describing the approval to initiate the resupply; and
storing the signed electronic document in an electronic repository.

4. The computer-implemented method of claim 1, further comprising automatically generating the event relating to resupply of one or more medical items for the patient, without human intervention.

5. The computer-implemented method of claim 4, wherein the generating the event is based on at least one of: (i) policy rules relating to resupply of the one or more medical items or (ii) prior resupply orders relating to the one or more medical items.

6. The computer-implemented method of claim 1, further comprising:
identifying a second event relating to a second resupply of a second one or more medical items for a second patient, wherein the second resupply requires approval from a second physician;
transmitting, based on the second event, a second request for electronic approval of the second resupply to an electronic healthcare system for the second physician;
receiving, in response to the second request, and indication of failure of electronic approval of the second resupply; and
declining to initiate, based on the indication of failure, resupply of the second one or more medical items.

7. The computer-implemented method of claim 6, further comprising:
determining a cause for the failure of electronic approval of the second resupply based on parsing a textual indication included in the response to the second request using natural language processing (NLP).

8. The computer-implemented method of claim 1, further comprising:
identifying the electronic healthcare system for the physician, from among a plurality of potential electronic healthcare systems.

9. The computer-implemented method of claim 8, wherein identifying the electronic healthcare system for the physician, from among the plurality of potential electronic healthcare systems, comprises:
transmitting an electronic message to each of the plurality of potential electronic healthcare systems, the electronic message comprising an identifier for the physician; and
receiving a response from the electronic healthcare system for the physician indicating that the physician is associated with the electronic healthcare system.

10. The computer-implemented method of claim 1, further comprising:
determining to transmit the request for electronic approval of the resupply to the electronic healthcare system for the physician based on determining that a date of a prior electronic approval by the physician falls within a threshold value.

11. The computer implemented method of claim 1, wherein transmitting the request for electronic approval occurs automatically without human intervention, and wherein initiating the resupply occurs automatically without human intervention.

12. An apparatus comprising:

a memory; and a hardware processor communicatively coupled to the memory, the hardware processor configured to perform operations comprising:

identifying an event relating to resupply of one or more medical items for a patient, wherein the resupply requires approval from a physician;

transmitting, based on the event, a request for electronic approval of the resupply to an electronic healthcare system for the physician;

receiving, in response to the request, an indication of failure of electronic approval of the resupply;

declining to initiate, based on the indication of failure, resupply of the one or more medical items; and determining a cause for the failure of electronic approval of the resupply based on parsing a textual indication included in the response to the request using natural language processing (NLP).

13. The apparatus of claim 12, wherein transmitting the request for electronic approval of the resupply to the electronic healthcare system for the physician further comprises:

determining that the electronic healthcare system for the physician is compatible with an application programming interface (API) request for approval of the resupply;

transmitting the API request for approval of the resupply; and receiving an API response indicating the indication of failure.

14. The apparatus of claim 12, further comprising automatically generating the event relating to resupply of one or more medical items for the patient, without human intervention.

15. The apparatus of claim 12, further comprising:

identifying a second event relating to a second resupply of a second one or more medical items for a second patient, wherein the second resupply requires approval from a second physician;

transmitting, based on the second event, a second request for electronic approval of the second resupply to a second electronic healthcare system for the second physician;

receiving a second response from the second electronic healthcare system for the second physician indicating approval for the second request; and initiating, based on the second response, resupply of the second one or more medical items, wherein the second one or more medical items are used to treat the second patient.

16. The apparatus of claim 12, further comprising:

identifying the electronic healthcare system for the physician, from among a plurality of potential electronic healthcare systems, comprising:

transmitting an electronic message to each of the plurality of potential electronic healthcare systems, the electronic message comprising an identifier for the physician; and receiving a response from the electronic healthcare system for the physician indicating that the physician is associated with the electronic healthcare system.

17. A non-transitory computer-readable medium comprising instructions that, when executed by a processor, cause the processor to perform operations comprising:

generating an event relating to resupply of one or more medical items for a patient, wherein the resupply requires approval from a physician;

transmitting, based on the event, a request for electronic approval of the resupply to an electronic healthcare system for the physician, comprising:

determining that the electronic healthcare system for the physician is compatible with an application programming interface (API) request for approval of the resupply;

dynamically generating an electronic document relating to the required approval;

providing the electronic document to the electronic healthcare system for the physician, comprising transmitting the API request for approval of the resupply; and receiving an electronic message response from the electronic healthcare system for the physician indicating approval for the request, comprising receiving an API response indicating the approval, wherein the electronic healthcare system for the physician is compatible with the request for electronic approval of the resupply; and initiating, based on the response, resupply of the one or more medical items, wherein the one or more medical items are used to treat the patient.

18. The non-transitory computer-readable medium of claim 17, wherein the API response indicating the approval provides a signed electronic document and one or more electronic data elements describing the approval.

19. The non-transitory computer-readable medium of claim 17, further comprising:

identifying a second event relating to a second resupply of a second one or more medical items for a second patient, wherein the second resupply requires approval from a second physician;

transmitting, based on the second event, a second request for electronic approval of the second resupply to an electronic healthcare system for the second physician;

receiving, in response to the second request, and indication of failure of electronic approval of the second resupply; and declining to initiate, based on the indication of failure, resupply of the second one or more medical items.

20. The non-transitory computer-readable medium of claim 17, further comprising:

identifying the electronic healthcare system for the physician, from among a plurality of potential electronic healthcare systems, comprising:

transmitting an electronic message to each of the plurality of potential electronic healthcare systems, the electronic message comprising an identifier for the physician; and receiving a response from the electronic healthcare system for the physician indicating that the physician is associated with the electronic healthcare system.

* * * * *